United States Patent [19]
Martins et al.

[11] Patent Number: 5,356,413
[45] Date of Patent: Oct. 18, 1994

[54] SURGICAL ANCHOR AND METHOD FOR DEPLOYING THE SAME

[75] Inventors: Harold M. Martins, Newton; John T. Rice, Lincoln, both of Mass.; Lonnie E. Paulos, Salt Lake City, Utah

[73] Assignee: Mitek Surgical Products, Inc., Norwood, Mass.

[21] Appl. No.: 30,657

[22] Filed: Mar. 12, 1993

[51] Int. Cl.$^5$ .............................................. A61B 17/00
[52] U.S. Cl. ........................................ 606/75; 606/72; 606/232
[58] Field of Search .................... 606/72, 73, 74, 75, 606/76, 77, 219, 220, 232

[56] References Cited

U.S. PATENT DOCUMENTS

| | | | |
|---|---|---|---|
| 4,997,433 | 3/1991 | Goble et al. | 606/64 |
| 5,147,362 | 9/1992 | Goble | 606/72 |
| 5,156,616 | 10/1992 | Meadows et al. | 606/73 |
| 5,236,445 | 8/1993 | Hayhurst et al. | 606/73 |

Primary Examiner—Stephen C. Pellegrino
Assistant Examiner—Sonya C. Harris
Attorney, Agent, or Firm—Pandiscio & Pandiscio

[57] ABSTRACT

An anchor for attaching an object to a bone-like structure, and a method for deploying same is provided. The anchor includes a body and a plurality of barbs. The barbs are located in axially aligned, circumferentially spaced relation to each other about the body. Each barb is elastically deformable, and has a normal configuration which extends rearwardly and radially outwardly from the body to an outer end located outside a longitudinal projection of the largest geometric cross-section of the body transverse to its longitudinal axis. A bore for engagement by a length of cord-like material extends through the front portion of the body. An opening oriented perpendicularly to the bore extends through the rear portion of the body. A longitudinal slot aligned with the opening connects the front end of the body to the opening. The slot minimizes the force necessary to pull the anchor into a preformed tunnel in the bone-like structure, and allows the anchor to be disconnected from the object and removed after deployment. The method includes the steps of threading cord-like material through the bore; attaching the object to the rear portion of the body; threading the cord-like material through the preformed tunnel; pulling the anchor into, and/or through, the preformed tunnel to a position slightly beyond its desired anchoring location; and exerting a pulling force on the object to set the outer ends of the barbs into the bone-like structure.

24 Claims, 5 Drawing Sheets

SURGICAL ANCHOR AND METHOD FOR DEPLOYING THE SAME

FIELD OF THE INVENTION

The present invention relates generally to fastening devices. More particularly, the invention relates to devices for attaching portions of objects within tunnels formed in bones or bone-like structures, and to methods for the deployment of such devices.

BACKGROUND OF THE INVENTION

The complete or partial detachment of ligaments, tendons or other soft tissues from their associated bones within the body are relatively commonplace injuries, particularly among athletes. Such injuries are generally the result of excess stress being placed on these tissues. Tissue detachment may occur as the result of an accident such as a fall, overexertion during a work related activity, during the course of an athletic event or in any one of many other situations and/or activities.

In the case of a partial detachment, commonly referred to under the general term "sprain", the injury will frequently heal itself, if given sufficient time, and if care is taken not to expose the injury to any undue stress during the healing process. If, however, the ligament or tendon is completely detached from its associated bone or bones, or if it is severed as part of a traumatic injury, partial or permanent disability may result. Fortunately, a number of surgical techniques exist for reattaching such detached tissues and/or completely replacing severely damaged tissues.

One such technique involves the reattachment of the detached tissue using "traditional" attachment devices such as metal staples, sutures over buttons and cancellous bone screws. Such "traditional" attachment devices have also been used to attach tendon or ligament substitutes (often formed of autogenous tissue harvested from elsewhere in the body) to the desired bone or bones.

Another technique is described in detail in U.S. Pat. No. 4,950,270 entitled "Cannulated Self-Tapping Bone Screw", issued to Bowman et al. on Aug. 21, 1990, which patent is specifically incorporated herein by reference. In this technique, the anterior cruciate ligament in a human knee, for example, is replaced and/or repaired by forming bone tunnels through the tibia and/or femur at the points of normal attachment of the anterior cruciate ligament. A ligament graft with a bone block on at least one of its ends is sized to fit within the bone tunnels. Suture is then attached to the outer end of each bone plug and thereafter passed through the femoral and/or tibial bone tunnels. The femoral plug and/or the tibial plug is (are) then inserted into the appropriate bone tunnel behind the suture. Subsequently, the suture is drawn tight (simultaneously in opposite directions, in cases where bone plugs are to be located in both a femoral bone tunnel and a tibial bone tunnel). This procedure positions the bone plug (or plugs) in the desired position, and imparts the desired degree of tension to the ligament or ligament substitute. Finally, a bone screw is inserted between each bone plug and the wall of its associated bone tunnel so as to securely lock the bone plug in position by a tight interference fit.

Alternatives to the foregoing use of bone screws are also well known in the art. For example, in U.S. Pat. No. 5,147,362 entitled "Endosteal Ligament Fixation Device" issued Sep. 15, 1992 to E. Marlowe Goble, rearwardly extending flexible barbs or pins are attached to the bone plug (either directly or by a collar, cap or similar intervening element) for anchoring a bone plug within a bone tunnel. The disclosure of the foregoing U.S. Pat. No. 5,147,362 is also incorporated herein by reference.

Similarly, in U.S. Pat. No. 4,997,433 entitled "Endosteal Fixation Stud and System" issued Mar. 5, 1991 to E. Marlowe Goble et al., a device is disclosed for attachment to the outer end of the bone plug. The device includes a pair of spaced, forwardly projecting, flexible arms. One of these arms includes a substantially rigid, radially and rearwardly projecting portion disposed adjacent its outer end. This device is adapted for insertion through a bone tunnel ahead of the bone plug such that the projection may engage the outer surface of the bone adjacent the far end of the bone tunnel. This projection acts to maintain the position of the bone plug within the bone tunnel so long as rearwardly directed tension is maintained on the repair material. The disclosure of U.S. Pat. No. 4,997,433 is also incorporated herein by reference.

It will be understood that repair methods of the types described above have not been uniformly successful. For example, rigid attachment using "traditional" attachment devices such as staples, sutures and screws often cannot be maintained even under normal tensile loads.

Also, the use of sharp screws to create a locking interference fit between a bone plug and a bone tunnel introduces problems. For one thing, there is always the possibility of damaging the ligament or repair material during insertion of the screw. In addition, it can be difficult to maintain the desired tension on the ligament or repair material during insertion of the screw. Also, the insertion of the screw requires that a twisting motion be imparted to the screw; this twisting motion can in turn cause rotation of the bone plug in the bone tunnel, and may lead to undesirable twisting of the ligament which is attached to the bone plug.

The removal of such bone screws can also cause problems. In those cases in which the screw can be removed simply by unscrewing it in the usual manner, an undesirable hole is left in the bone. In many cases, however, the screw cannot be simply unscrewed from the bone to remove it. In these situations, the screw must typically be either forceably pulled out of the bone or it must be removed by chipping away the surrounding bone. Both of these procedures can cause serious damage to the bone.

The foregoing attachment devices of U.S. Pat. Nos. 5,147,362 and 4,997,433 are also not totally satisfactory. This is because in the device of U.S. Pat. No. 5,147,362, the cross-sectional size of the bone tunnel must significantly exceed the cross-sectional size of the bone plug on account of the constructions utilized. This results in the bone plug being separated from the sidewall of the bone tunnel by a substantial gap, thereby slowing the assimilation of the plug into the bone during healing. The device of U.S. Pat. No. 4,997,433, on the other hand, is limited to use in a particular method of reattachment. Further, undesirable binding between the stud and the sidewall of the bone tunnel may occur as the stud's projection is forced through the bone tunnel.

Various types of suture anchors and anchors for attaching objects to bone are also well known in the art. A number of these devices are described in detail in U.S. Pat. Nos. 4,898,156; 4,899,743; and 4,968,315 (each of which being presently owned by Mitek Surgical Products, Inc., of Norwood, Mass., the assignee of this application). The disclosures of these patents are also incorporated herein by reference.

OBJECTS OF THE INVENTION

Accordingly, one object of the present invention is to provide a surgical anchor useful in the repair and/or replacement of ligaments, tendons and the like in a procedure wherein at least one free end of the repair or replacement material is affixed within a bone tunnel such that the repair is held in place under tension, without danger of severing, twisting and/or otherwise damaging the replacement or repair material, and with minimal damage to the sidewalls of the bone tunnel.

Another object of the present invention is to provide a surgical anchor which is adapted to maintain repair or replacement material in close proximity to the sidewall of a bone tunnel in a manner which promotes the growth of a permanent attachment between the repair or replacement material and the bone.

Still another object of the present invention is to provide a surgical anchor which minimizes the amount of force required to set the anchor within a bone tunnel.

Yet another object of the present invention is to provide a surgical anchor including simple and convenient means for attaching a bone plug or other portion of a ligament, tendon or similar repair material thereto.

Another object of the present invention is to provide an improved method for repairing and/or replacing ligaments, tendons or similar tissue by affixing the ends of such tissue (or its replacement) within bone tunnels so as to promote the biological fixation of such tissue to the bone.

Yet another object of the present invention is to provide a surgical anchor useful in affixing an end of an object within a bone tunnel, where the anchor includes means to facilitate detachment of the tissue from the anchor, and removal of the anchor from the bone tunnel.

SUMMARY OF THE INVENTION

These and other objects are achieved by the use of the present invention, which comprises a novel surgical anchor and the use of the same. The novel surgical anchor generally comprises a coupling member and a plurality of barbs.

The coupling member comprises a body having a longitudinal axis, a front end, a front portion adjacent the front end, a flattened rear portion and an outer surface. Connection means are associated with the front portion of the body for connecting the body to anchor pulling means, and attachment means are associated with the rear portion of the body for attaching the body to the repair material—namely, a bone plug, detached tissue, or to a replacement for the detached tissue.

In the preferred embodiment of the invention, the connection means comprises a first transverse opening which extends through the front portion of the body, and the anchor pulling means comprises a first length of strong suture, braided twine, wire or the like adapted to be threaded through the first transverse opening. The attachment means comprises a second transverse opening which extends through the flattened rear portion of the body. The second transverse opening is oriented substantially perpendicular to the first transverse opening. The second transverse opening may be adapted to have a free end of a tendon, ligament or other elongated, non-rigid piece of tissue or tissue substitute looped therethrough so as to allow the piece of tissue or tissue substitute to be attached to the anchor. Alternatively, the second transverse opening may be adapted to have a second length of strong suture, braided twine, wire or the like threaded therethrough. The second length of suture or the like may then be attached to a free end of a tendon, ligament or other non-rigid piece of tissue or tissue substitute, or it may be attached to a bone plug or block which is itself attached to a free end of a tendon, ligament or other non-rigid piece of tissue or tissue substitute.

A longitudinal slot extends forwardly from the second transverse opening, through the front portion of the body, so as to open on its front end. This slot allows the front portion of the anchor body to flex inwardly during deployment, so as to help minimize the insertion forces required to set the anchor. This slot also provides access to the material looped through the second transverse opening so as to permit the anchor to be disengaged from the material if the same should be desired after anchor deployment.

In addition to the foregoing, the body has at least one set of identical longitudinal channels, each having its forward end located the same axial distance from the front end of the body. The channels are located in equally circumferentially spaced relation to each other about the outer surface of the body.

The barbs are also located in substantially equally spaced circumferential relation to each other about the outer surface of the body. In the preferred embodiment, one barb extends outwardly and rearwardly from the forward end of each longitudinal channel to an outer end which is located radially outwardly of an axial projection of the largest geometrical cross-section of the body (as taken transverse to its longitudinal axis). Each barb is capable of being elastically deformed such that it will lie substantially within the channel with which it is associated.

In the method of the invention, the first length of suture-like material is threaded through the first transverse opening, and a free end of the ligament, tendon or the like, or a bone plug attached to that free end, is attached to the rear portion of the anchor body. As noted above, in the case where the repair material constitutes soft tissue such as a ligament, tendon or the like, the soft repair material may be attached directly to the anchor body by looping it through the second transverse opening, or by attaching it to the second transverse opening via an intervening piece of suture or the like. Alternatively, in the case where the repair material constitutes a rigid element such as a bone plug or block at a free end of a ligament, tendon or the like, the repair material may be attached to the anchor body via an intervening piece of suture, etc.

In any case, once the repair material has been attached to the anchor body, the free ends of the first length of suture-like material are inserted through a bone tunnel which is to receive the repair material. Thereafter, the anchor is pulled into and then along the bone tunnel by pulling on the free ends of the first length of suture. As this occurs, the anchor's barbs will yieldably engage the surrounding bone so as to permit the anchor, and hence the repair material, to be deployed at a desired position. It will be understood by those skilled in the art that the anchor may be set either (1) completely within the bone tunnel, such that the outer ends of the barbs dig into the sidewall of the bone tunnel when tension is applied to the repair material (hereinafter referred to as "endosteal fixation"), or (2) partially emerging from the bone tunnel, such that the outer ends of the barbs dig into the outer surface of the bone adjacent the far side of the bone tunnel when tension is applied to the repair material (hereinafter referred to as "cortical fixation").

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein.

DETAILED DESCRIPTION OF THE PREFERRED EMBODIMENT

Figure 1:
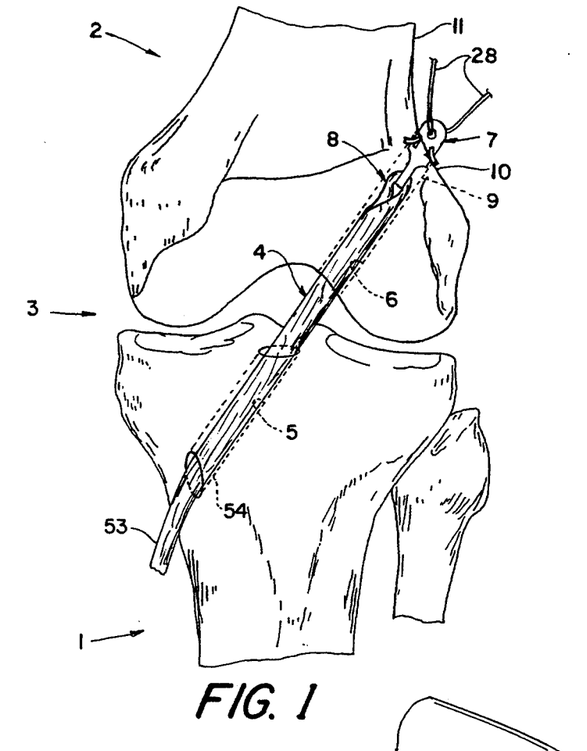
FIG. 1 is a view showing a portion of a human femur bone and a portion of a human tibia bone, each having a bone tunnel therethrough, and showing a surgical anchor formed in accordance with the present invention, wherein the anchor has its barbs cortically engaging the surface of the femur bone and its rear portion directly attached to an end of a ligament located in the bone tunnels.

In order to establish a frame of reference for the following detailed description of the preferred embodiment of the surgical anchor and its method of use, FIG. 1 shows a view of a portion of a human tibia 1 and a portion of a human femur 2 at the point at which they meet to form a human knee joint, generally indicated at 3. The knee joint 3 is stabilized by a number of connecting tissues (generally not shown in the drawings for purposes of clarity) such as the patellar tendon, the quadriceps femuris tendon, the lateral and medial collateral ligaments, and the anterior and posterior cruciate ligaments. An anterior cruciate ligament graft 4 is shown extending through a tibial bone tunnel 5 and into a femoral bone tunnel 6. A surgical anchor 7, formed in accordance with the present invention, is shown attached directly to the end 8 of ligament 4 which is located within femoral bone tunnel 6. Anchor 7 extends through the outer end 9 of femoral bone tunnel 6 so as to cortically engage the portion 10 of the outer surface 11 of femur 2 which is located adjacent to outer end 9 of femoral bone tunnel 6.

Figure 5:
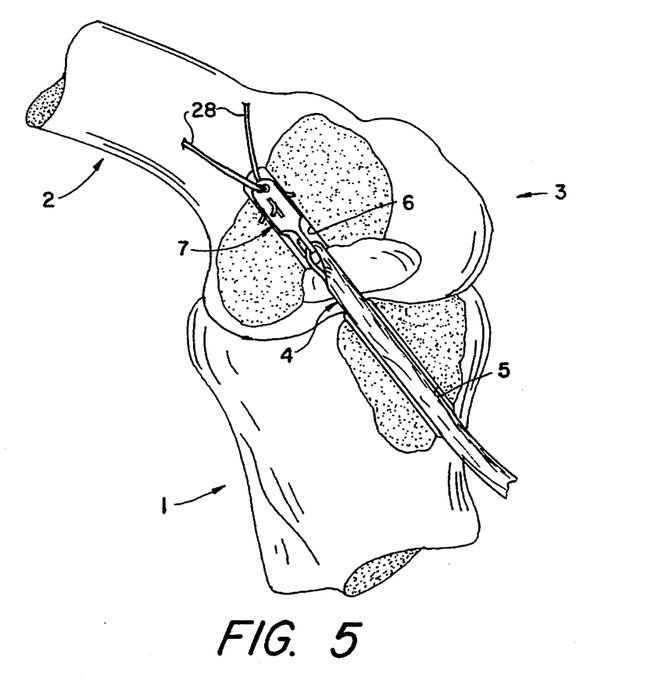
FIG. 5 is a view showing a portion of a human femur bone and a portion of a human tibia bone, each having a bone tunnel therethrough, and showing a surgical anchor formed in accordance with the present invention, wherein the anchor has its barbs endosteally engaging the sidewall of the femoral bone tunnel and its rear portion directly attached to an end of a ligament located in the bone tunnels.
Figure 6:
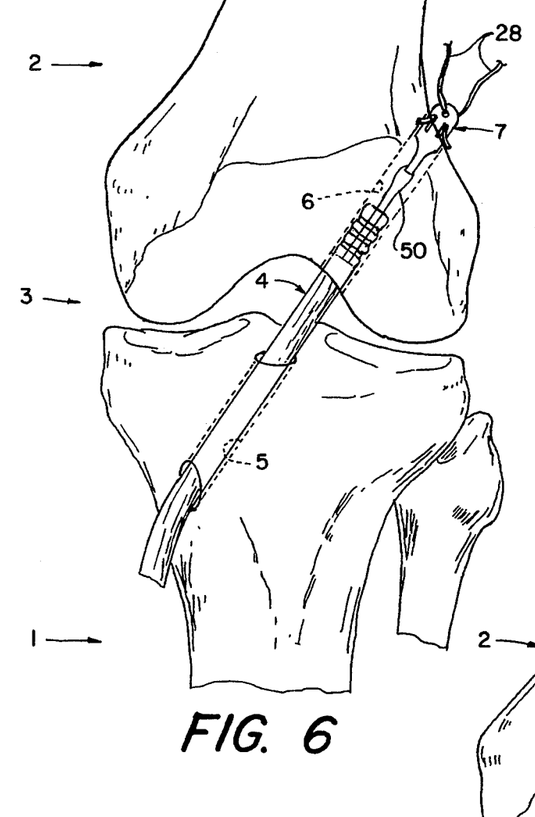
FIG. 6 is a view similar to that of FIG. 1, except that the end of the ligament is shown attached to the rear portion of the surgical anchor by an intervening length of suture-like material.
Figure 7:
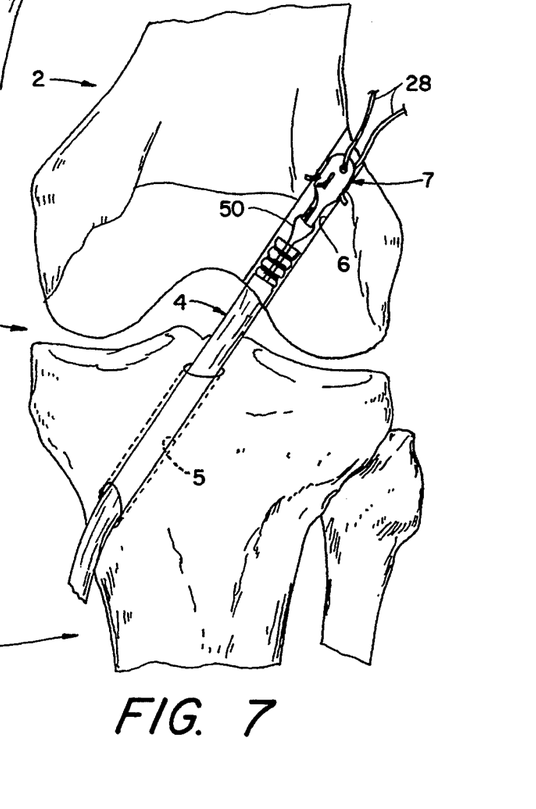
FIG. 7 is a view similar to that of FIG. 6, except that the surgical anchor is shown endosteally positioned in the femur.
Figure 8:
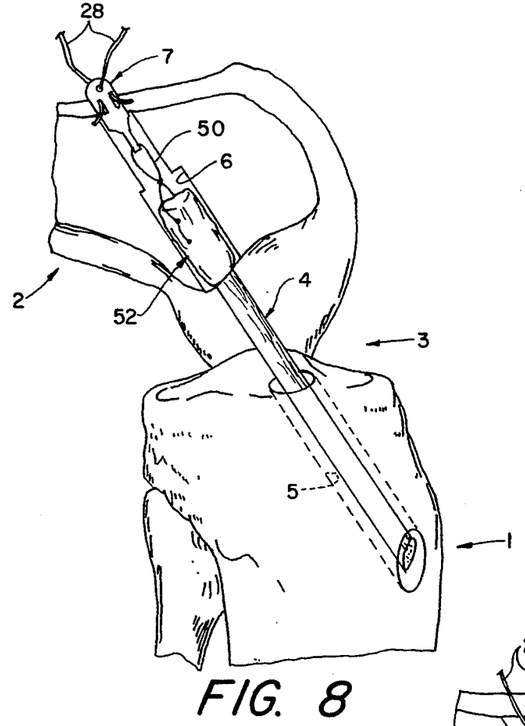
FIG. 8 is a view showing a portion of a human femur bone and a portion of a human tibia bone, each having a bone tunnel therethrough, and showing a surgical anchor formed in accordance with the present invention, wherein the anchor has its barbs cortically engaging the surface of the femur bone and its rear portion attached by an intervening length of suture-like material to a bone plug located at an end of a ligament disposed in the bone tunnels.
Figure 9:
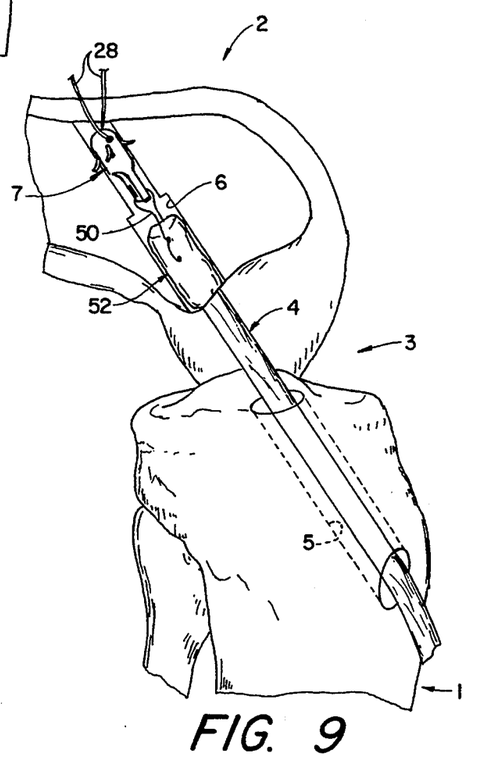
FIG. 9 is a view similar to that of FIG. 8, except that the surgical anchor is shown endosteally positioned in the femur.

It is, of course, also to be understood that the repair or replacement of ligaments, tendons and the like may require the endosteal fixation of the anchor to the bone (see FIG. 5); or that the repair material be attached to the anchor by means of an intervening piece of suture or the like (see FIGS. 6 and 7, showing such an arrangement in the context of cortical and endosteal fixation, respectively). Furthermore, it is to be understood that the repair or replacement of ligaments, tendons and the like may require the attachment of a bone plug or block to the bone (see FIGS. 8 and 9, showing such an arrangement in the context of cortical and endosteal fixation, respectively). It is contemplated that the present anchor will be used in all of these situations, as will hereinafter be discussed in further detail.

Figure 2:
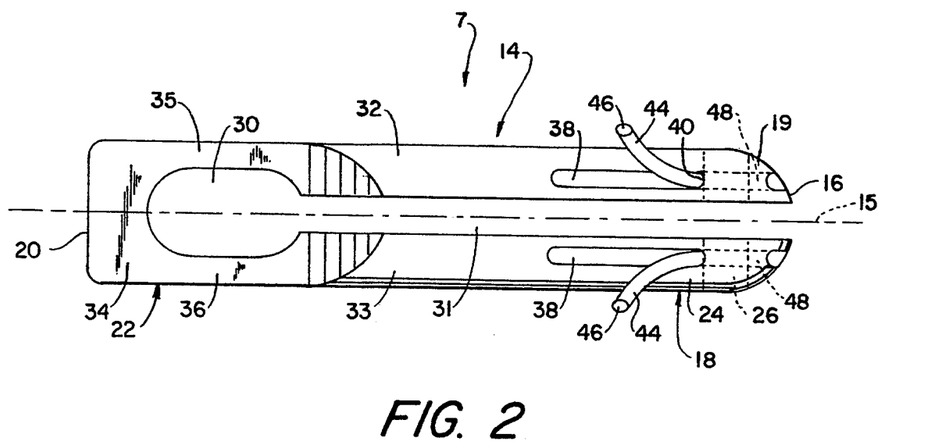
FIG. 2 is a side view of the surgical anchor of the present invention.
Figure 3:
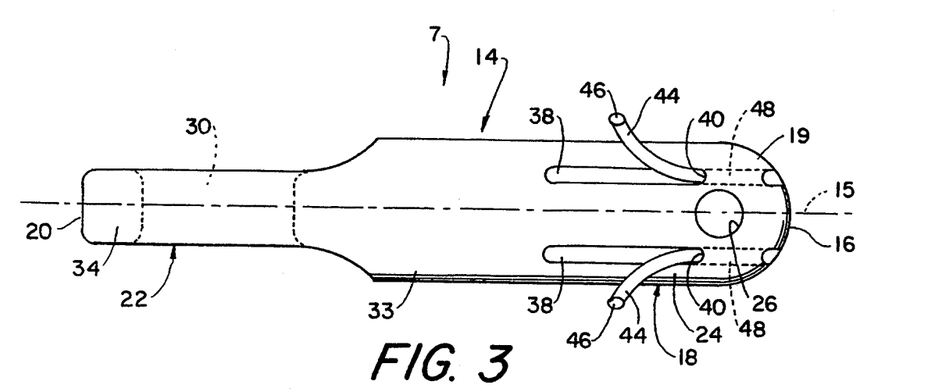
FIG. 3 is a side view of the surgical anchor shown in FIG. 2, wherein the anchor has been rotated 90° about its longitudinal axis from the position shown in FIG. 2.
Figure 4:
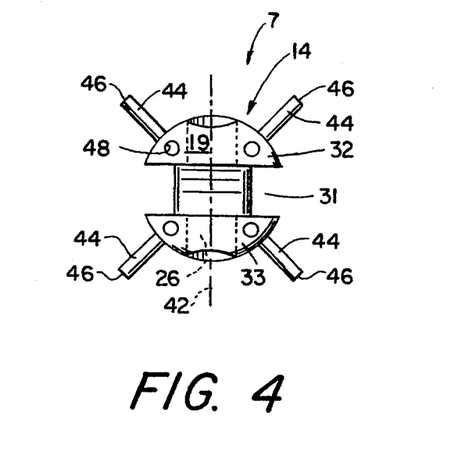
FIG. 4 is a front end view of the surgical anchor shown in FIG. 2.

Referring next to FIGS. 2, 3 and 4, surgical anchor 7 comprises a body 14 having a longitudinal axis 15, a front end 16, a front portion 18 adjacent front end 16, a rear end 20, and a rear portion 22 adjacent rear end 20. The outer surface 24 of front portion 18 defines a generally semi-spherical surface 19, thereby providing the body with a generally forwardly pointed configuration. In the preferred embodiment of the invention, body 14 is formed of 6AL-4V ELI titanium. It is to be understood, however, that body 14 could also be formed out of any other suitable, rigid biocompatible metal, or any suitable biocompatible polymeric material, or any suitable bioabsorbable material, all without departure from the present invention.

A bore 26 extends diametrically through the body's front portion 18 transverse to longitudinal axis 15. Bore 26 is sized such that a strong suture 28 (see FIGS. 1 and 5–9), or some other suitable pulling means, may be threaded therethrough for pulling anchor 7 in a forward axial direction. In addition, tapered grooves (not shown) may extend forwardly from the entries of bore 26 into body 14. These grooves, combined with the rounding of the edges of the entries of bore 26 into body 14, provide a smooth, substantially continuous surface against which the pulling means (e.g. suture 28) may bear. This feature reduces the chance of breaking the pulling means during the deployment of the anchor.

The rear portion 22 of body 14 includes an opening 30 extending transversely through body 14 generally adjacent its rear end 20. Opening 30 is oriented in body 14 substantially perpendicular to bore 26 in front portion 18. Further, opening 30 is sized to directly receive either a loop of ligament, tendon or the like (see FIGS. 1 and 5) or a loop of suture which is attached to a ligament, tendon or the like (see FIGS. 6 and 7) or which is attached to a bone block or plug (see FIGS. 8 and 9).

In the embodiment shown in FIGS. 2–4, rear portion 22 is flattened adjacent rear end 20, and opening 30 extends through the flattened section. The edges of the entries of opening 30 into the anchor body are also preferably rounded to minimize the chance of tissue or suture damage or breakage during the anchor insertion process. Further, the flattening of rear portion 22 relative to the remainder of the anchor provides a pathway for the tissue or suture which will extend rearwardly from opening 30 when the anchor is being deployed within a bone tunnel. This pathway allows the tissue or suture to extend along the flattened sides of the anchor while the anchor is positioned within a bone tunnel so that the tissue or suture is not crushed between the anchor and the sidewall of the bone tunnel. This feature is particularly important in the case where the tissue (or its synthetic substitute) is connected directly to the anchor by looping the tissue through opening 30 (i.e., in the manner shown in FIGS. 1 and 5).

A longitudinal slot 31 extends from opening 30 to front end 16 of body 14. Slot 31 is also oriented substantially perpendicularly to bore 26, and extends across the entire diameter of body 14. On account of this construction, body 14 forms a pair of spaced, parallel arms 32 and 33 which extend from the rearmost portion 34 of the body to its front end 16. Arms 32 and 33 are connected to rearmost portion 34 by opposing portions 35 and 36, respectively, adjacent opening 30. Portions 35 and 36 have a smaller transverse cross-section than the remainder of arms 32 and 33. In view of this construction, arms 32 and 33 will tend to flex inwardly about portions 35 and 36 when inwardly-directed forces are applied to arms 32 and 33 adjacent front end 16 of body 14. The importance of this feature to the overall operation of the device will become more fully apparent in view of the following description.

Front portion 18 of body 14 further includes at least two equally circumferentially spaced longitudinal channels 38 formed in each of the arms 32 and 33. Longitudinal channels 38 all terminate in a forward end 40. Forward ends 40 are all located substantially the same distance from front end 16. In the particular structure shown in FIGS. 2–4, two longitudinal channels 38 are formed in the outer surface of each of the arms 32 and 33. These channels are circumferentially spaced 90° from each other, that is, at a 45° angle from the opposite sides of a plane 42 (FIG. 4) containing longitudinal axis 15 of body 14.

A plurality of barbs 44 extend outwardly and rearwardly from body 14, in spaced circumferential relation to each other. In the preferred embodiment shown in FIGS. 2–4, one such barb 44 extends outwardly and rearwardly from the forward end 40 of each of the channels 38 to an outer end 46. Each outer end 46 is normally located radially outside the periphery of an axial projection of the maximum geometric cross-section of body 14, as taken transverse to the longitudinal axis 15 of the body. At the same time, however, barbs 44 are formed out of an elastically deformable material such that outer ends 46 can be forced radially inwardly so as to be located within the periphery of an axial projection of the maximum geometric cross-section of body 14. On account of this construction, when anchor 7 is inserted longitudinally into an appropriately sized bone tunnel, the outer ends 46 of barbs 44 will engage and be deflected inwardly by the sidewall of the bone tunnel. This yieldable engagement of barbs 44 with the adjacent bone permits the anchor to be moved along the bone tunnel and then fixed in position, either fully within the bone tunnel (i.e., "endosteally") or at the point where the bone tunnel exits the bone (i.e., "cortically"), as will hereinafter be discussed in further detail.

In the preferred embodiment, barbs 44 are preferably formed out of a pseudoelastic material of the type disclosed in U.S. Pat. No. 4,665,906 entitled "Medical Devices Incorporating SIM Alloy Elements", issued May 19, 1987 to Jervis, which patent is specifically incorporated herein by reference. By way of example, one such pseudoelastic material might be a nickel titanium alloy such as Nitinol, which is available from Flexmedics of Minneapolis, Minn., among others. The use of such a material, in combination with the normal orientation of the barbs relative to the anchor body, allows the barbs to "spring back" toward their normal, unstressed condition after the insertion process is complete.

In the preferred embodiment, barbs 44 are formed as curved arcs extending outwardly from body 14 when in their normal, unstressed condition. Each barb 44 preferably forms an arc of approximately 90 degrees, with the length of the barb being selected so that when one end of the barb is inserted in a longitudinal bore 48 extending forwardly from the forward end 40 of a channel 38, the other end 46 of the barb will extend the desired distance outwardly from body 14. In this respect it will also be appreciated that the forced fit of the curved barb within the straight bore 48, combined with the elastic memory of the barb, will tend to maintain the barb in place within the bore. At the same time, the sides of channel 38 also help prevent the wire from twisting within the bore. The body of anchor 7 may also be crimped adjacent the bores 48 so as to further ensure the locking engagement of the barbs with body 14.

It is to be appreciated that the lengths (and widths) of barbs 44 and longitudinal channels 38 are carefully sized relative to one another, such that barbs 44 may be fully received in longitudinal channels 38 to the extent necessary when the barbs are deformed during anchor deployment.

In view of the foregoing, it will be seen that when a pulling means such as suture 28 (see, for example FIG. 1) is threaded through bore 26 and the anchor is thereafter pulled into a bone tunnel using the same, the pulling means will tend to impart a moderate compressive force on the front portions of arms 32 and 33. This compressive force may or may not be sufficient by itself to cause visible compression of the front ends of the arms. As the insertion process proceeds further, however, barbs 44 will engage the sidewall of the bone tunnel. This engagement will force the outer ends 46 of the barbs 44 inward and rearward, so as to fold the barbs back into their associated channels 38. At the same time, this engagement of the barbs with the sidewall of the bone tunnel will have the effect of providing a further, even greater, compressive force to the front portions of the arms 32 and 33. This combination of compressive forces will cause the front portions of arms 32 and 33 to move inward to some extent, thereby carrying the barbs inward with them, and thus reducing the total amount of barb deformation required to pass the anchor down the bone tunnel. This has the effect of significantly easing passage of the anchor through the bone tunnel. Thus it will be seen that by providing the slot 31 in the anchor, the total amount of force required to deploy the anchor within a bone tunnel will be reduced, as compared to a similar anchor which does not have a slot 31.

Slot 31 also provides an important additional advantage, in that it makes it very easy to detach the anchor from the tissue or bone plug to which it is attached, even while the anchor is deployed in a bone. Specifically, the longitudinal slot 31 provides a passageway for the insertion of a sharp tool to sever the tissue or suture which is looped through the anchor's opening 30. In particular, when the anchor has been set cortically as shown in FIGS. 1, 6 and 8, its front portion 18 will project out of the far side of the bone tunnel. In that case, a thin cutting tool (not shown) may be passed directly through slot 31 to engage and sever the tissue (see FIG. 1) or the suture (see FIGS. 6 and 8) looped through the anchor's opening 30. Alternatively, when the anchor has been set endosteally as shown in FIGS. 5, 7 and 9, the thin cutting tool may be passed down the bone tunnel and then through the slot 31 so as to engage and sever the tissue (see FIG. 5) or suture (see FIGS. 7 and 9) looped through the anchor's opening 30. Of course, in either case, once the anchor has been released from the repair material which is connected to the rearmost portion of its body, the anchor may be pulled out of the bone tunnel.

It will be understood by those skilled in the art that the dimensions of anchor 7 will vary according to use. Solely for purposes of illustration, exemplary dimensions of one anchor formed according to the present invention are set forth below:

| | |
|---|---|
| Maximum diameter | 0.232 inches |
| Length | 1.181 inches |
| Diameter of bore 26 | 0.078 inches |
| Length of opening 30 | 0.250 inches |
| Width of opening 30 | 0.157 inches |
| Radius of curvature front portion 18 | 0.110 inches |
| Length of channels 38 | 0.240 inches |
| Width of channels 32 | 0.033 inches |
| Width of flattened section | 0.125 inches |
| Number of barbs | 4 |
| Width of slot 31 | 0.060 inches |

Anchor 7 may be used in a variety of ways. First it will be described in the context of replacing an anterior cruciate ligament 4, where the tissue is to be attached directly to the anchor and the anchor is to be cortically fixed to the femur. More particularly, and looking now at FIG. 1, a length of strong suture or similar material 28 is threaded through bore 26 in front portion 18 of anchor 7. If desired, the free ends of suture 28 may be knotted together so as to form a loop with which to pull anchor 7. A length of ligament or replacement tissue 4 is then attached to the rear portion of anchor 7. This is accomplished by threading a free end of the ligament or replacement material 4 through opening 30 in the anchor body, and then fastening it down to the trailing portion of the repair or replacement material (e.g. by suturing) in the manner shown in FIG. 1. Then the suture 28, which is attached to the front end of anchor 7, is threaded through the tibial and femoral bone tunnels 5 and 6, respectively. Bone tunnels 5 and 6 are sized so as to be just slightly larger than the maximum diameter of body 14, whereby the anchor's barbs 44 may properly engage the sidewalls of bone tunnels 5 and 6. Thereafter, the outer ends of suture 28 are pulled so as to draw anchor 7 (and with it, its trailing ligament 4) through tibial bone tunnel 5 and into femoral bone tunnel 6. It will be understood that the generally forwardly pointed configuration of the anchor facilitates its entry into and through the bone tunnels. As the anchor is pulled through the bone tunnels, its barbs 44 yieldably engage the sidewalls of the bone tunnels, deflecting inwardly so as to permit the anchor to pass down the bone tunnels. At the same time, arms 32 and 33 also flex inwardly to some extent, so as to help reduce the total amount of barb deflection required to allow the anchor to pass along the bone tunnels. The anchor is pulled through femoral bone tunnel 6 to the point where at least some, if not all, of its barbs 44 pop free of bone tunnel 6. Thereafter, a pulling force is exerted on the opposite end 53 of ligament 4 to firmly set the barbs into the outer surface layer of the femur so as to effect the desired cortical fixation. Suture 28 may then be pulled free from the set anchor. Finally, the other end 53 of ligament 4, projecting from the outer end 54 of tibial bone tunnel 5, is affixed to the tibia. This may be accomplished by using another anchor 7 appropriately attached to ligament 4 or, alternatively, it may be attached to the end 53 of tibia 1 in any one of the many ways well known in the art. By way of example, if the other end 53 of ligament 4 consists solely of soft tissue, the tissue may be attached to the tibia by staples, screws and the like. On the other hand, if the other end 53 of ligament 4 includes a bone block, the block can be attached to the tibia using an interference screw. Such attachments are of the sort well known in the art.

Looking next at FIG. 5, it is also anticipated that anchor 7 might be used to replace an anterior cruciate ligament 4, where the tissue is attached directly to the anchor and the anchor is endosteally fixed to the femur. In this case the procedure used is identical to the procedure just described with respect to FIG. 1, except that when drawing anchor 7 through femoral bone tunnel 6, the pulling on suture 28 stops when the anchor is still entirely within the femur. In this way anchor 7 will be endosteally fixed to femur 2. Again, a slight rearward force is applied to the opposite end 53 of ligament 4 once the anchor is in position within the femur, so as to securely fix the anchor to the femur. The opposite end 53 of ligament 4 may then be fixed to tibia 1 in the manner previously discussed.

Anchor 7 may also be used to replace an anterior cruciate ligament 4, where the tissue is not attached directly to the anchor. More particularly, and looking now at FIG. 6, the procedure used for cortical fixation is identical to the procedure described above with respect to FIG. 1, except that when attaching ligament 4 to anchor 7, an intervening length of suture 50 is used to connect ligament 4 to anchor 7. This is typically done by wrapping suture 50 several times around the end of the ligament which is being attached to anchor 7, and then looping suture 50 through anchor opening 30 before fixing it to ligament 4.

A similar arrangement can also be used to effect an endosteal fixation, as shown in FIG. 7.

Looking next at FIG. 8, it is also anticipated that anchor 7 might be used to replace an anterior cruciate ligament, where a bone block is attached to the anchor and the anchor is cortically fixed to the femur. In this case the procedure used is identical to the procedure described above with respect to FIG. 1, except that a length of suture 50 is used to connect bone block 52 to anchor 7. This is typically done by passing suture 50 through one or more holes formed in bone block 52, and then looping suture 50 through anchor opening 30 one or more times before making it fast. It will be appreciated that in a fixation of the sort illustrated in FIG. 8, the size of bone tunnel 6 is coordinated with the size bone block 52 so as to assure a close fit between the femur and the bone block. At the same time, the size of bone tunnel 6 is coordinated with the size of anchor 7 so as to permit proper engagement of barbs 44 with the walls of the bone tunnels. In some situations this may call for the use of a stepped bone tunnel 6, such as that shown in FIG. 8.

Looking next at FIG. 9, it is also anticipated that one might use a similar arrangement to effect an endosteal fixation.

Numerous variations, modifications, adjustments, alterations and alternative uses of the present invention will occur to those skilled in the art in view of the foregoing description of an exemplary and illustrative embodiment of the invention.

Thus, for example, while in the preferred embodiment barbs 44 are formed with a normally curved configuration which is then deformed during anchor deployment toward a straight configuration, it is contemplated that barbs 44 might be formed with a normally straight configuration which is then deformed during anchor deployment toward a curved configuration. Of course, in such a modification, bores 48 would have to have their orientations altered somewhat so as to normally direct the straight barbs outwardly and rearwardly from the front of the anchor.

Figure 10:
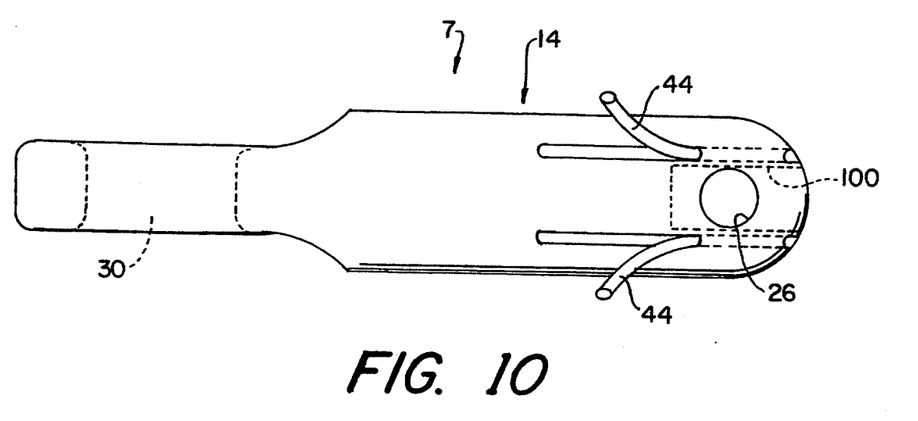
FIG. 10 is a view like that of FIG. 3, except that it shows a threaded bore 100 added to the front end of anchor 7.

Furthermore, means such as a threaded bore 100 (see FIG. 10) might be provided at the front end of the anchor. The presence of such a threaded bore allows the anchor to be securely engaged by a counterpart threaded tool (not shown) for repositioning purposes. This can be particularly important if the anchor must be repositioned after it has been set endosteally in a bone tunnel and the pulling means (i.e., suture 28) has already been removed from the anchor, as it invariably is at the conclusion of the anchor deployment procedure.

Also, the foregoing description has generally focused on the anchor's barbs being either wholly outside (i e., "cortical" fixation) or wholly within (i e., "endosteal" fixation) a bone tunnel It is to be understood, however, that it is the end of the repair tissue which must be disposed within the bone tunnel, and not necessarily the anchor itself. Hence, it is emphasized that the barbs of the anchor may all be lodged wholly within the bone tunnel, some of the barbs may engage the sidewall of the bone tunnel while others rest upon the surface of the bone adjacent the end of the bone tunnel, or all the barbs may rest against the last described surface, depending upon the surgical procedure involved. Each of these alternatives is considered to be within the scope of the present invention in its broadest aspects.

It will be further understood that this specification is intended to be illustrative only, and in no way limiting of the invention. The only limitations of the breadth and scope of this invention are set forth in the appended claims.

What is claimed is:

1. A surgical anchor for attaching an object to a bone-like structure defining a tunnel therein, said anchor comprising:

a coupling member adapted for longitudinal insertion into said tunnel, and a plurality of barbs attached to said coupling member in axially aligned, circumferentially spaced relation to one another;

said coupling member comprising a body having a longitudinal axis, a maximum cross-section transverse to said longitudinal axis, an outer surface, a front end, a front portion adjacent said front end, a rear end, a rear portion adjacent said rear end defining an opening extending therethrough, a slot aligned with said longitudinal axis and extending from said opening to said front end, and connection means associated with said front portion, said front end and said front portion together defining a generally forwardly pointed configuration, and said connection means being adapted for releasable engagement by anchor pulling means; and each said barb being elastically deformable, including an outer end, and being attached to said coupling member forwardly of said opening such that each said barb normally extends rearwardly and radially outwardly from said outer surface with said outer end of each said barb being normally located outwardly of an axial projection of said maximum transverse cross-section of said body, and such that each said barb is elastically deformable into a configuration located substantially within said axial projection.

2. The surgical anchor of claim 1 wherein:

said body defines a plurality of longitudinal channels, each said channel including a forward end, said channels being located in axially aligned, circumferentially spaced relation to one another about said outer surface of said body; and one of said plurality of barbs extends rearwardly and radially outwardly from each said forward end of each said channel.

3. The surgical anchor of claim 2 wherein each of said barbs is curved in its normal unstressed state, but is deformable to a substantially straight configuration generally within said axial projection.

4. The surgical anchor of claim 1 wherein said connecting means comprises a bore extending substantially transversely through said front portion perpendicular to said longitudinal slot, and said pulling means comprises a length of suture-like material extending through said bore.

5. The surgical anchor of claim 1 wherein said front end and said front portion of said body together comprise a forwardly facing, substantially semi-spherical portion of said outer surface.

6. The surgical anchor of claim 1 wherein said barbs are formed of wire.

7. The surgical anchor of claim 6 wherein said wire is made of a pseudoelastic shape memory material.

8. The surgical anchor of claim 7 wherein said pseudoelastic shape memory material is a nickel-titanium alloy.

9. The surgical anchor of claim 1 wherein a first portion of said outer surface of said body is associated with said rear portion, a second portion of said outer surface of said body is associated with said front portion, and at least a part of said first portion of said outer surface is relieved relative to said second portion of said outer surface.

10. A method of affixing a free end of an object to a bone-like structure defining a tunnel therein, said method comprising the steps of:

(a) providing a surgical anchor comprising a coupling member adapted for longitudinal insertion into said tunnel, and a plurality of barbs attached to said coupling member in axially aligned and circumferentially spaced relation to one another;

said coupling member comprising a body having a longitudinal axis, a maximum cross-section transverse to said longitudinal axis, an outer surface, a front end, a front portion adjacent said front end, a rear end, a rear portion adjacent said rear end defining an opening extending therethrough, a slot aligned with said longitudinal axis and extending from said opening to said front end, and connection means associated with said front portion, said front end and said front portion of said body together defining a generally forwardly pointed configuration, and said connection means being adapted for releasable engagement by anchor pulling means; and each said barb being elastically deformable, including an outer end, and being attached to said coupling member forwardly of said opening such that each said barb normally extends rearwardly and radially outwardly from said outer surface with each said outer end being normally located outwardly of an axial projection of said maximum transverse cross-section of said body, and such that each said barb is elastically deformable into a configuration located substantially within said axial projection;

(b) providing a first length of suture-like material having a pair of free ends, and connecting a portion of said first length of suture-like material located between said free ends to said connecting means;

(c) attaching said free end of said object to said rear portion of said body;

(d) threading said free ends of said first length of suture-like material through said tunnel; and (e) pulling on said free ends of said suture-like material extending through said tunnel so as to thereby draw said anchor and said free end of said object into said tunnel.

11. The method of claim 10 wherein said object comprises an elongate, non-rigid element having at least one free end and a body portion, and said attaching step is accomplished by threading said at least one free end of said elongate, non-rigid element through said opening in said coupling member body, and thereafter affixing said at least one free end of said elongate, non-rigid element to said body portion of said elongate, non-rigid element.

12. The method of claim 10 wherein said object comprises an elongate, non-rigid element and said attaching step is accomplished by providing a second length of suture-like material having a first end and a second end, threading said first end of said second length of suture-like material through said opening and affixing said first end and said second end of said second length of suture-like material to said free end of said object.

13. The method of claim 10 wherein said object comprises an elongate, non-rigid element and said attaching step is accomplished by providing a second length of suture-like material having a first end and a second end, threading said first end of said second length of suture-like material sequentially through said opening and said free end of said object, and thereafter knotting said first and second ends of said second length of suture-like material together.

14. The method of claim 13 wherein a bone block is attached to said free end of said object, and said first end of said second length of suture-like material is passed through said bone block prior to knotting said first and second ends of said second length of suture-like material together.

15. The method of claim 10 wherein said tunnel comprises a sidewall, said anchor is drawn to a position wholly within said tunnel, and thereafter a pulling force is applied to said object so as to set said barbs into said sidewall of said tunnel.

16. The method of claim 10 wherein said tunnel comprises a first end and a second end, said anchor is drawn into said first end of, and through, said tunnel to a position such that at least some of said plurality of barbs are located outwardly of said second end of said tunnel, and thereafter a pulling force is applied to said object so as to set said outwardly located barbs into said bone-like structure adjacent said second end of said tunnel.

17. The method of claim 10 wherein:

said body defines a plurality of longitudinal channels, each said channel including a forward end, said channels being located in axially aligned, circumferentially spaced relation to one another about said outer surface of said body; and one of said plurality of barbs extends rearwardly and radially outwardly from each said forward end of each said channel.

18. The method of claim 17 wherein each of said plurality of barbs is curved in its normal unstressed state, but is elastically deformable to a substantially straight configuration generally within said axial projection.

19. The method of claim 10 wherein said connecting means comprises a bore extending substantially transversely through said front portion perpendicular to said longitudinal slot, and said pulling means comprises a length of suture-like material extending through said bore.

20. The method of claim 10 wherein said front portion and said front end of said body together comprise a forwardly facing, substantially semi-spherical portion of said outer surface.

21. The method of claim 10 wherein said barbs are formed of wire.

22. The method of claim 21 wherein said wire is made of a pseudoelastic shape memory material.

23. The method of claim 22 wherein said pseudoelastic shape memory material is a nickel-titanium alloy.

24. The method of claim 10 wherein a first portion of said outer surface of said body is associated with said rear portion, a second portion of said outer surface of said body is associated with said front portion, and at least a part of said first portion of said outer surface aligned with said opening is relieved relative to said second portion of said outer surface.

* * * * *